US007940976B2

(12) United States Patent
Ozawa (10) Patent No.: US 7,940,976 B2
(45) Date of Patent: May 10, 2011

(54) X-RAY IMAGE DIAGNOSIS APPARATUS AND A METHOD FOR GENERATING IMAGE DATA

(75) Inventor: Masahiro Ozawa, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 901 days.

(21) Appl. No.: 11/851,700

(22) Filed: Sep. 7, 2007

(65) Prior Publication Data

US 2008/0063250 A1 Mar. 13, 2008

(30) Foreign Application Priority Data

Sep. 7, 2006 (JP) ................................ P2006-242893

(51) Int. Cl.
*G06K 9/00* (2006.01)
*H05G 1/70* (2006.01)
(52) U.S. Cl. ............................ 382/132; 382/275; 378/92
(58) Field of Classification Search .................. 382/128, 382/129, 130, 131, 132, 133, 134, 168, 181, 382/194, 199, 216, 232, 254, 274, 275, 276, 382/285–289, 296, 305, 312; 600/426, 407; 378/21, 62, 207, 205, 92
See application file for complete search history.

(56) References Cited

U.S. PATENT DOCUMENTS

| | | | | |
|---|---|---|---|---|
| 7,142,633 B2 * | 11/2006 | Eberhard et al. | ................ | 378/62 |
| 7,186,023 B2 * | 3/2007 | Morita et al. | ................ | 378/207 |
| 7,267,482 B2 * | 9/2007 | Ohishi | ................ | 378/205 |
| 7,519,412 B2 * | 4/2009 | Mistretta | ................ | 600/407 |
| 7,570,791 B2 * | 8/2009 | Frank et al. | ................ | 382/132 |
| 7,606,613 B2 * | 10/2009 | Simon et al. | ................ | 600/426 |
| 7,844,094 B2 * | 11/2010 | Jeung et al. | ................ | 382/131 |

FOREIGN PATENT DOCUMENTS

JP 2004-8304 1/2004

* cited by examiner

*Primary Examiner* — Seyed Azarian
(74) *Attorney, Agent, or Firm* — Oblon, Spivak, McClelland, Maier & Neustadt, L.L.P.

(57) ABSTRACT

An X-ray image diagnosis apparatus and a method for generating three dimensional image data of a moving body based on a plurality of two dimensional pixel data of the moving body that are automatically collected at different angle positions, wherein a plurality of radiography angle positions is previously designated, and the two dimensional pixel data is generated in correspondence with data of an object, e.g., a waveform of an electrocardiogram, collected at a real time. Based on the vital data, rotating movements for collecting a plurality of pixel data are decided. When a plurality of two dimensional pixel data obtained in correspondence with a plurality of heart beat cycles, for example, is collected at a certain designated angle position, the radiography position is automatically moved to a next collecting angle position. A set of a plurality of two dimensional pixel data collected at the same phase of the vital data of the moving body is selected for generating three dimensional image data.

12 Claims, 6 Drawing Sheets

X-RAY IMAGE DIAGNOSIS APPARATUS AND A METHOD FOR GENERATING IMAGE DATA

CROSS-REFERENCE TO RELATED APPLICATIONS

This application claims priority under 37 C.F.R. §119 from Japanese Patent Application No. 2006-242893, filed on Sep. 7, 2006, the contents of which are expressly incorporated herein by reference in their entirety.

BACKGROUND OF THE INVENTION

1. Field of the Invention

The present invention relates to an X-ray image diagnosis apparatus and a method for generating image data and, in particular to an X-ray image diagnosis apparatus and a method for generating and displaying three dimensional image data based on a plurality of two dimensional pixel data that are collected by irradiating an object portion from different irradiation angle positions.

2. Description of the Related Art

Recently, in accordance with developments of an angiocardiogram inspection by using a catheter or an IVR (Interventional Radiology), an X-ray image diagnosis apparatus is widely used for diagnosis or treatments in circulatory organ areas. Such an X-ray image diagnosis apparatus for circulatory organs is used for performing diagnosis or treatments by using three dimensional images, e.g., of a coronary tree, of a moving object, such as, for instance, a coronary artery of a heart or blood vessels of artery or intravenous in a whole body. Usually, for an X-ray image diagnosis of blood vessels, an X-ray radiography is performed under a condition in which a radiocontrast agent is injected in blood vessels.

An X-ray image diagnosis apparatus for application to circulatory organs is generally constructed so that an X-ray radiography for a diagnosis portion of a blood vessel is performed at optimum angle positions by combining rotating movements of a supporting mechanism, such as a C-arm for supporting an X-ray generating unit and X-ray detecting unit and position movements of a top plate for supporting an object. To obtain three dimensional image data of a periodically moving blood vessel, such as a coronary artery, through an X-ray image diagnosis apparatus, a radiocontrast agent is injected into a blood vessel of the irradiation object. During a state in which the radiocontrast agent is present in the injected blood vessel, a plurality of two dimensional pixel data are collected by performing X-ray radiography from different angle position. It has been proposed to generate a three dimensional image of a blood vessel by using a plurality of two dimensional pixel data among the collected plurality of two dimensional pixel data by referencing to the same phase of an object's heart beat. For instance, Japanese Patent Application Publication 2004-8304 is referred.

There are two types of X-ray image diagnosis apparatus for collecting a plurality of two dimensional pixel data. One is a bi-plane type X-ray image diagnosis apparatus, and the other is a single plane type X-ray image diagnosis apparatus. The bi-plane type X-ray image diagnosis apparatus includes double C-arms for respectively supporting an X-ray generating source and a penetrated X-rays detector. The double C-arms cross at different angles with respect to each other in order to collect a plurality of two dimensional pixel data by simultaneously radiating X-rays from the respective X-ray generating source onto a blood vessel of the object from the different angles. The single plane type X-ray image diagnosis apparatus includes a single C-arm only for supporting a pair of an X-ray generating source and a penetrated X-ray detector. To collect a plurality of two dimensional pixel data, the single plane type X-ray image diagnosis apparatus must rotate the single C-arm and irradiate X-rays on an object blood vessel from a plurality of different angle positions. Since the bi-plane type X-ray image diagnosis apparatus can perform X-ray radiography of an object blood vessel from different angles, it can easily collect a plurality of two dimensional pixel data at the same time while eliminating complex C-arm rotating movements as is characteristic of the single plane type apparatus. However, the bi-plane type apparatus is expensive and occupies a large floor area for setting up such a type of apparatus. On the contrary, since a single plane type X-ray image diagnosis apparatus does not need such a large floor area and its cost is much lower than that of the bi-plane type apparatus, it is now widely applied for performing an X-ray image diagnosis or X-ray image treatments of a moving object, such as a blood vessel, in view of three dimensional images (coronary tree) of the moving object.

To generate three dimensional images (coronary tree) of a blood vessel, one needs to select a plurality of two dimensional pixel data that are obtained at a same phase in vital data of an object among a plurality of two dimensional pixel data being collected at a plurality of different angle positions. However, as explained above, for a single plane type X-ray image diagnosis apparatus, it is necessary to move a C-arm supporting an X-ray generating source and an X-ray detector by performing rotations. Thus, a supporting C-arm is moved and rotated at a plurality of different angle positions so as to collect a plurality of two dimensional pixel data by performing X-ray radiography at a certain frame rate at the respective positions. Consequently, a plurality of two dimensional pixel data can not always be collected at a same phase in vital data from an object. Even if two dimensional pixel data of a same phase can be collected, the data are not always obtained at an appropriate difference between each of the plurality of angle positions of the C-arm for generating three dimensional images. Even if two dimensional pixel data of the same phase in vital data are collected at too small differences between the angle positions, errors or distortions easily occur between the collected pixel data of the same phase. This is a serious problem for generating three dimensional images from a plurality of two dimensional pixel data of the same phase. If a plurality of two dimensional pixel data of the same phase that are suitable for generating three dimensional image data are not collected during a first operation of X-ray radiography, it becomes necessary to perform additional X-ray radiography. To do so, it becomes necessary to again inject a radiocontrast agent into the object. This is also problematic since it places a severe burden on the object.

SUMMARY OF THE INVENTION

The present invention solves these defects and problems of the conventional single plane type X-ray image diagnosis apparatus. The X-ray image diagnosis apparatus in accordance with present invention can easily collect a plurality of two dimensional pixel data of the same phase that are imaged at a plurality of angle positions having sufficient angle differences so as to avoid occurrence of errors or distortions among pixel data. Thus, the present invention provides an X-ray image diagnosis apparatus and a method for generating image data that can easily generate and display three dimensional image data of moving objects.

In a single plane type X-ray image diagnosis apparatus and the image data generating method thereof according to the present invention, a plurality of X-ray radiography angle positions are previously designated so that at each angle positions an appropriate angle difference exists so as to avoid errors or distortions among pixel data that are collected through a plurality of X-ray radiography. At each of the designated angle positions, a plurality of two dimensional pixel data of heart beat cycles are collected based on vital signal data being supplied from an object in real time. When pixel data collection at a first angle position has been completed, a C-arm is automatically rotated to a next designated angle position. Data collection is thus successively performed and a three dimensional image data is generated by selecting two dimensional pixel data of the same phase among the collected plurality of pixel data. According to the present invention, a plurality of sets of two dimensional pixel data of the same phase are displayed in order to select an appropriate set of two dimensional pixel data that is suitable for generating three dimensional image data. Consequently, it becomes possible to easily achieve a generation and a display of three dimensional image data of a moving body.

Thus, according to one aspect of the present invention, there is provided an X-ray image diagnosis apparatus including: a paired X-ray generating unit configured to radiate X-rays on an object and an X-ray detecting unit configured to detect X-rays penetrated through the object and to generate X-ray projection data; an angle position setting unit configured to set at least two different radiography angle positions in a successive sequence for imaging the object by moving the paired X-ray generating unit and the X-ray detecting unit; a controller configured to control moving and performance of radiography operations of the paired X-ray generating unit and X-ray detecting unit based on angle position data supplied from the angle position setting unit and periodic vital data acquired from the object; a pixel data processing unit configured to generate a plurality of two dimensional pixel data using X-ray projection data supplied from the X-ray detecting unit positioned at the at least two different radiography angle positions during a time corresponding to at least more than one cycle of vital data; and a three dimensional image data generating unit configured to generate three dimensional image data using at least two of the two dimensional pixel data collected at a particular same phase of the vital data among the collected plurality of pixel data at each of the at least two different radiography angle positions generated by the pixel data processing unit.

According to another aspect of the present invention, the X-ray image diagnosis apparatus as above described may include: a set searching unit configured to search and combine at least more than two of two dimensional pixel data of a particular phase of vital data as one set among a plurality of pixel data generated from the pixel data processing unit; a reduced pixel data generating unit configured to generate reduced pixel data of the respective pixel data in each set of pixel data provided through the set searching unit and to recognize each of the reduced pixel data as a set; a display unit configured to display each of the reduced pixel data of a set recognized as a set in the reduced pixel data generating unit; and a selection unit configured to select a desired set of the reduced pixel data among a plurality of reduced pixel data displayed on the display unit; whereby the three dimensional image data generating unit generates three dimensional image data by using pixel data corresponded to the selected set of the reduced pixel data selected by the selection unit.

According to another aspect of the present invention, the X-ray image diagnosis apparatus as above described may include: set searching unit configured to combine at least more than two pixel data as one set among two dimensional pixel data generated in the image data generating unit based on a particular same phase of the vital data; a reduced pixel data generating unit configured to generate reduced pixel data of each set of pixel data combined in the set searching unit and to recognize each of the reduced pixel data as a set; a display unit configured to display each set of the reduced pixel data recognized as a set; and a selecting unit configured to select a desired set among a plurality of sets displayed on the display unit; wherein the three dimensional image data generating unit generates three dimensional image data by using pixel data corresponding to reduced pixel data of a set selected by the selecting unit.

According to a further aspect of the present invention, there is provided a method for generating X-ray image data, including: designating a plurality of different radiography angle positions for performing radiography by a paired X-ray source and an X-ray detector through an object; acquiring vital data of the object in a real time; collecting pixel data of at least more than one cycle of the vital data at a first position of the designated plurality of different radiography angle positions in correspondence with the vital signal data; rotating the pair of the X-ray source and the X-ray detector to a next angle position so as to collect next pixel data of at least more than one cycle of the vital data; selecting a set of pixel data of a particular same phase of the vital data among a plurality of pixel data collected at the plurality of different angle positions; and generating three dimensional image data using the selected set of the pixel data.

According to another aspect of the present invention, there is provided a method for generating image data, including: setting a paired X-ray generating unit for irradiating X-rays onto an object and X-ray detecting unit for detecting X-rays penetrated through the object and generating X-ray projection data at least at two different radiography angle positions; generating pixel data at least at the two different radiography angle positions that correspond to n cycles (n is a positive number of more than one) of vital data of an object using X-ray projection data collected through the X-ray detecting unit set at least at the two different radiography angle positions in correspondence with periodic vital data of the object; and generating three dimensional image data by using pixel data of a particular phase in the vital data among pixel data generated in the pixel data generating unit at least at two different radiography angle positions.

BRIEF DESCRIPTION OF THE DRAWINGS

The accompanying drawings, which are incorporated in and constitute part of this specification, illustrate various embodiments and/or features of the present invention, and together with the description, serve to explain the present invention. Where possible, the same reference number is used throughout the drawings to describe the same or like parts. In the drawings:

FIG. 2 is an exemplary waveform of an electrocardiogram from an object. In order to generate three dimensional image data, a plurality of two dimensional pixel data having the same phase in the wave form of a electrocardiogram shown in FIG. 2 are collected in the embodiment of an X-ray image diagnosis apparatus illustrated in FIG. 1.

DESCRIPTION OF THE PREFERRED EMBODIMENTS

Figure 1:
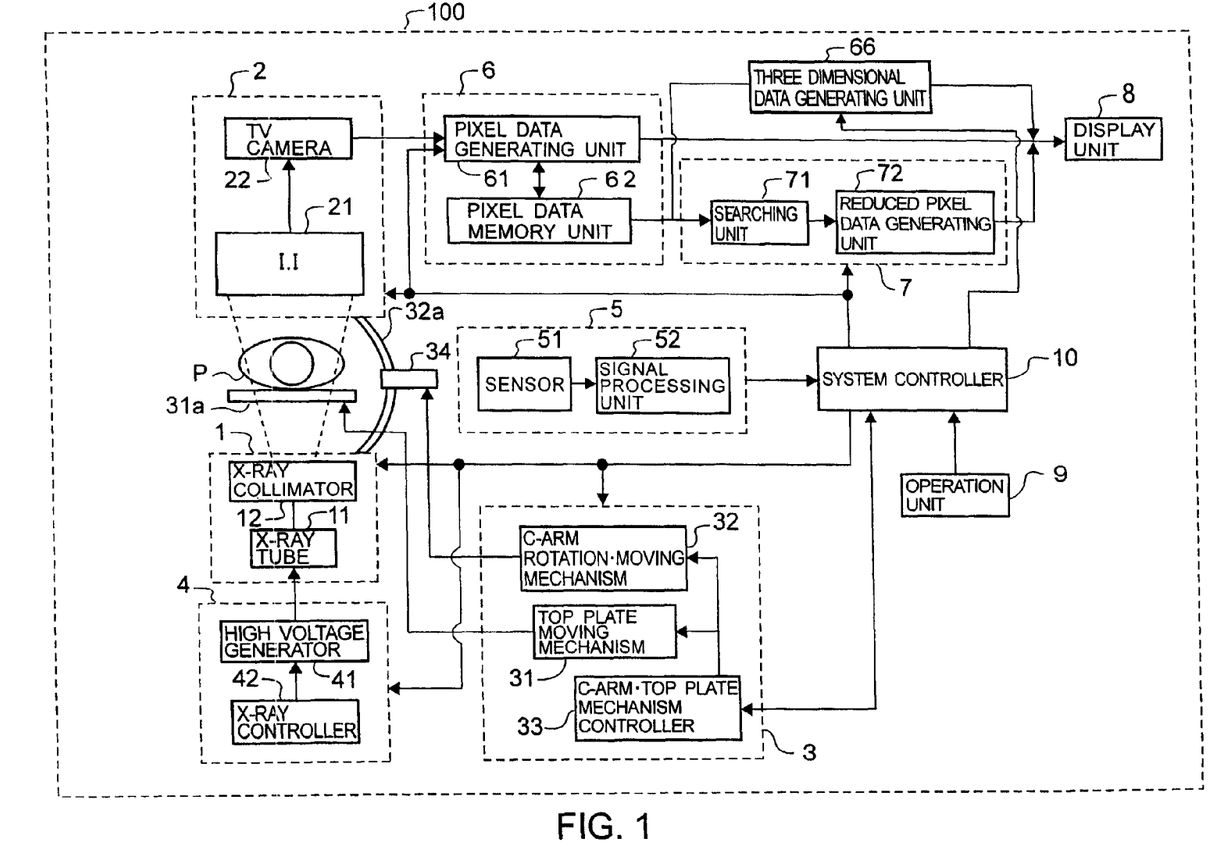
FIG. 1 is a block diagram illustrating one embodiment of a construction of a single plane type X-ray image diagnosis apparatus in accordance with the present invention.

Referring now to the drawings, FIG. 1 illustrates one embodiment of construction of a single plane type X-ray image diagnosis apparatus 100 in accordance with the present invention. The X-ray image diagnosis apparatus 100 includes an X-ray generating unit 1 for irradiating X-rays onto an object P and an X-ray detecting unit 2 for collecting X-ray projection data by two dimensionally detecting X-rays penetrated through an object P. The X-ray generating unit 1 and the penetrated X-ray detecting unit 2 are respectively supported at opposed edge portions of the C-arm 32a. The X-ray image diagnosis apparatus 100 further includes a drive unit 3 for implementing rotating movements of C-arm 32a and position movements of top plate 31a in order to support an object P and a high voltage generating unit 4. The high voltage generating unit 4 supplies a high voltage sufficient for irradiation of X-ray to the X-ray generating unit 1.

The drive unit 3 includes a top plate moving mechanism 31, a C-arm rotating/moving mechanism 32 and a C-arm/top plate mechanism controller 33 for controlling movements of both mechanisms 31 and 32. The top plate moving mechanism 31 moves the top plate 31a for supporting an object P along a body axis direction, a width direction of the top plate and up and down. The C-arm rotating/moving mechanism 32 performs rotation movements of C-arm 32a around an object P. C-arm 32a supports the X-ray generating unit 1 and the penetrated X-ray detecting unit 2. The C-arm/top plate mechanism controller 33 controls each operations of the respective movements of the top plate moving mechanism 31 and movements or rotations of the C-arm rotating/moving mechanism 32 based on control signals supplied from the system controller 10 so as to position an imaging object, such as blood vessel, and X-ray radiation unit at a plurality of different angle positions in order to perform X-ray radiography at appropriate angle positions while avoiding obstacles, such as bones, as explained later.

The top plate moving mechanism 31 includes a sensor (not shown), such as an encoder, for detecting a moved distance of the top plate 31a. C-arm/top plate mechanism controller 33 controls the top plate moving mechanism 31 based on the detected signals supplied from the moved distance sensor. The top plate moving mechanism 31 moves the top plate 31a so as to set it at desired positions based on the control signals from the C-arm/top plate mechanism controller 33. Similarly, C-arm rotating/moving mechanism 32 includes a rotating angle sensor, such as an encoder for detecting rotated angles of the C-arm 32a. C-arm rotating/moving mechanism 32 is rotated the C-arm under controlling from the C-arm/top plate mechanism controller 33 based on the detected living body signals supplied from the rotated angle sensor. By the rotations of the C-arm 32a, a pair of the X-ray generating unit 1 and the X-ray detecting unit 2 is positioned at desired radiography angle positions based on the controlling signals from the C-arm/top plate mechanism controller 33. When the C-arm 32a is positioned at a desired position, the C-arm rotating/moving mechanism 32 supplies an angle positioned signal of the positioned radiography angle position to the system controller 10.

The X-ray generating unit 1 includes an X-ray tube 11 for generating X-rays and an X-ray collimator 12. The X-ray diaphragm 12 restricts an X-ray irradiation area over an object P from the X-ray tube 11. A high voltage generating unit 4 supplies a high voltage to the X-ray tube 11 in X-ray generating unit 1. The high voltage generating unit 4 includes a high voltage generating unit 41 and an X-ray controller 42 that controls the high voltage generating 41 based on control signals supplied from a system controller 10.

X-ray detecting unit 2 includes an image intensifier (I.I.) 21 that detects X-rays penetrated through an object P and converts the penetrated X-rays to light signals, a television (TV) camera 22 for converting the light signals to electric signals and an A/D converter (not shown) for converting electric signals from the TV camera 22 to digital signals. X-ray projection data converted to digital signals are thereby supplied to a pixel data processing unit 6. I.I. 21 includes a moving mechanism so as to move its positions forward and backward so as to face the X-ray generating unit 1. Thus, a distance between the X-ray generating source and the X-ray detector (Source to Detector Distance: SDD) can be adjusted. Further adjustment can be made to the X-ray incidence view size (Field Of View: FOV) by controlling electric voltages of an X-ray receiving surface electrode of I.I. 21. In this embodiment, an I.I. is illustrated as a detector. It is, of course, possible to apply a plate surface type detector (Flat Panel Detector: FPD) in order to convert the detected X-rays to electric charges.

Pixel data processing unit 6 generates pixel data from X-ray projection data that are generated in the X-ray detecting unit 2. The generated pixel data are stored. Thus, the pixel data processing unit 6 includes a pixel data generating unit 61 for generating pixel data and a pixel data memory unit 62 for storing the generated pixel data. Pixel data generating unit 61 generates pixel data in accordance with X-ray radiography data being supplied from the detector 2 and managing vital data of an object P being supplied from a vital data measuring unit 5 through a system controller 10, as later explained. The generated pixel data are stored in a pixel data memory unit 62.

Pixel data that are collected at least at two different angle positions and stored in the pixel data memory unit 62 are supplied to a three dimensional image generating unit 66. The three dimensional image generating unit 66 generates three dimensional image data from pixel data collected at least at two different positions. To generate three dimensional image data, vital data are supplied from the system controller 10 in order to select pixel data of the same phase at least two different positions. The generated three dimensional data is displayed on a display unit 8.

The X-ray image diagnosis apparatus 100 further includes a pixel data searching unit 7 for searching a plurality of pixel data stored in the pixel data memory unit 62. Pixel data searching unit 7 includes a searching unit 71 for searching a plurality of pixel data of the same phase among a plurality of pixel data stored in the pixel data memory unit 62, and a reduced pixel data generating unit 72 for generating reduced pixel data of the searched pixel data of the same phase. A plurality of sets of the generated reduced pixel data of the same phase are displayed on a screen of a display unit 8. Thus, either a plurality of sets of pixel data of the same phase that are generated in the three dimensional image data generating unit 66 or a plurality of sets of reduced pixel data reduced of the same phase that are generated in the pixel data generating unit 72 are displayed on the display unit 8.

The X-ray image diagnosis apparatus 100 further includes an operation unit 9 for inputting various setting conditions or commands. The operation unit 9 designates various inputs of radiography conditions, such as, input operations of an object ID, such as a name of an object P and respective times of radiography, image magnifying ratio, designation of setting positions of the C-arm, designation of setting position of radiography angles, designation of setting position of the top plate, and a selection of static images or successive images that are collected at a time series during a certain time period (hereinafter, simply referred to as "a motion image"), and various conditions for displayings. In order to select a motion image, the operation unit 9 further inputs additional radiography conditions of a frame rate indicating a frame number in a unit time and an irradiation time. The system controller 10 totally controls the overall operation of the apparatus in accordance with the inputted conditions from the operation unit 9.

A vital data measuring unit 5 for detecting vital data of an object P includes a sensor 51 attached to an object P and a signal processing unit 52 for converting the signals detected by the sensor 51 into digital signals and for generating vital data. The vital data generated in the signal processing unit 52 are outputted to the system controller 10. The sensor 51 detects same phase portions among periodic motions of a moving body in an object under diagnosis. There are various types of the sensors in accordance with purpose of diagnosis. For instance, an electrocardiogram (ECG) signal sensor is applied to detect ECG waveforms for performing X-ray image diagnosis of a heart blood vessel. A brain wave sensor is used for an X-ray image diagnosis of blood vessels. A breath waveform sensor is applied for an X-ray image diagnosis of abdomen blood vessels. As an example, the present embodiment uses an ECG signal sensor 51 for performing an X-ray image diagnosis of periodically moving blood vessels, such as a coronary artery. In the embodiment, it is supposed that the signal processing unit 52 supplies phase data of R waves in ECG signals as the vital data.

Figure 2:
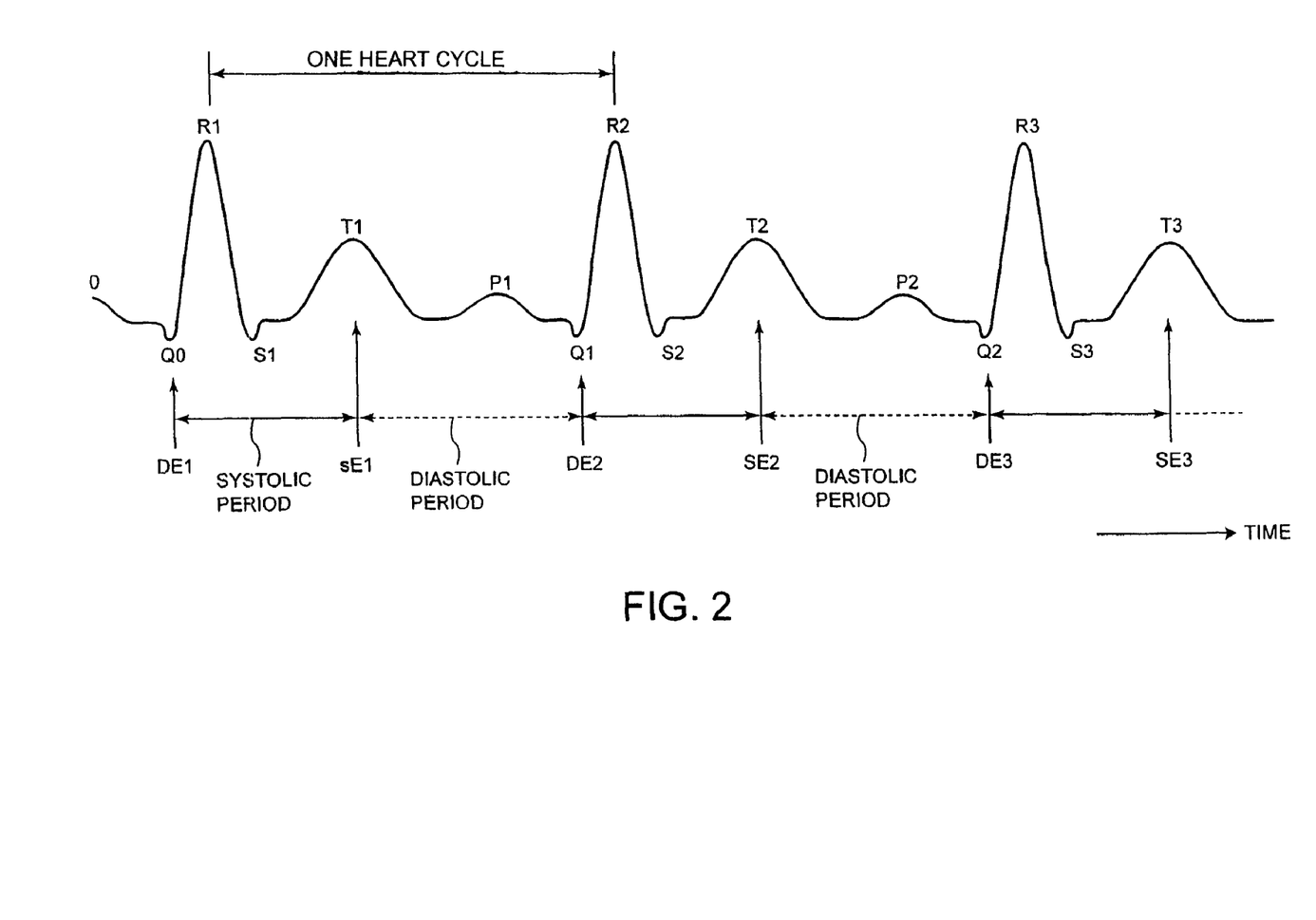

FIG. 2 illustrates a waveform of general ECG signals. One heart cycle of an object P is calculated as an interval between neighboring R waves, for example, as shown R1-R2 in FIG. 2. ECG signals include P waves, Q waves, S waves and T waves. As shown in FIG. 2, a time interval from a time DE1 of Q0 wave to a time SE1 of T1 wave is a systolic period. A time interval from a time SE1 of T1 wave to DE2 of Q1 wave is a diastolic period. To perform an X-ray image diagnosis of a periodically moving artery, it is possible to detect a diastolic end period. The X-ray image diagnosis apparatus in accordance with the present invention can basically use either one of P waves, Q waves, S waves and T waves as managing vital data. In this embodiment, pixel data is generated by detecting neighboring portions of R waves since it is easily detectable as vital data.

To perform a static image radiography, static image radiography conditions, such as, an object data, radiography times, an image magnifying ratio, radiography angle positions and top plate positions, are inputted from the operation unit 9. Based on the inputted static image radiography conditions, the system controller 10 supplies control signals to the high voltage generating unit 4. Upon receiving the control signals, the high voltage generating unit 4 supplies a high voltage to the X-ray generating unit 1. The X-ray generating unit 1 irradiates 1 shot of X-ray in order to generate image data for one frame.

To perform a motion image radiography, motion image radiography conditions, such as, an object data, radiography times, an image magnifying ratio, top plate positions, a plurality of radiography angles, a frame rate and irradiation times are inputted through the operation unit 9. Based on the inputted motion image radiography conditions, the system controller 10 supplies control signals to the high voltage generating unit 4. Upon receiving the control signals, the high voltage generating unit 4 supplies a plurality of high voltage pulses during a predetermined irradiation time at each of the designated plurality of radiography angle positions. Due to the plurality of high voltage pulses supplied from the high voltage generating unit 4, the X-ray generating unit 1 generates X-rays at each of the designated radiography angle positions in order to make up image data of a frame number that is constructed by multiplying the irradiation time by the frame rate.

In either case of a static image radiography or a motion image radiography, the distance SDD between the X-ray generating unit 1 and the X-ray detector 2 is set at the most appropriate position against a radiography object portion based on the control signals supplied from the system controller 10.

Figure 3A:
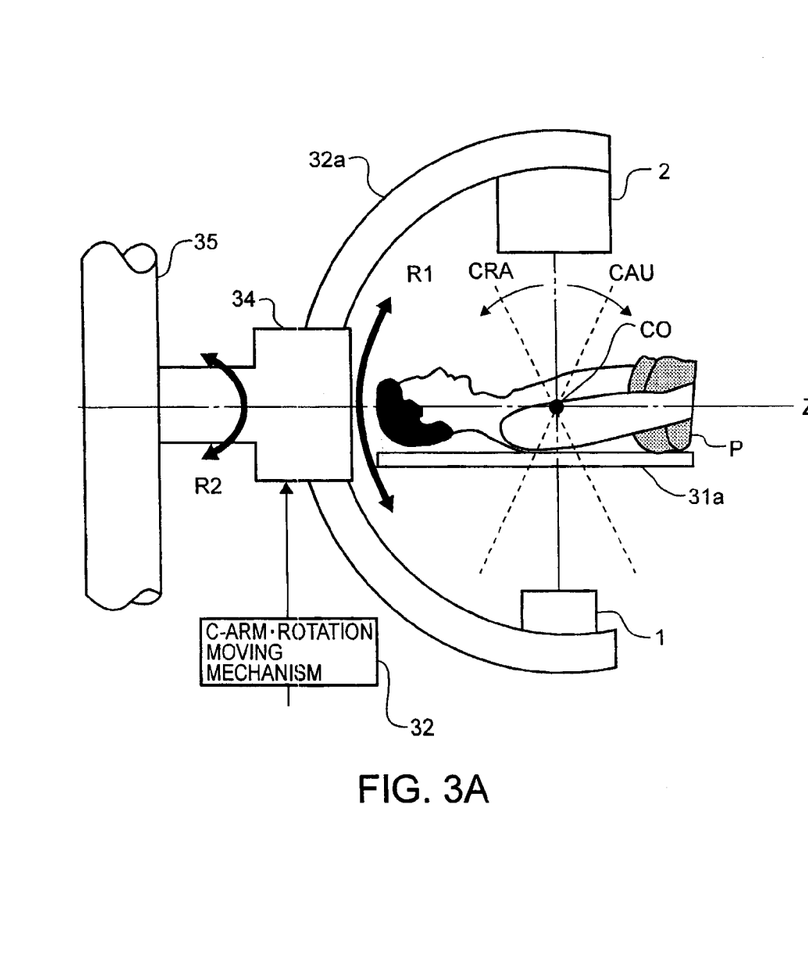
FIG. 3A is a side view illustrating a rotation movement of a C-arm in order to collect a plurality of two dimensional pixel data from a plurality of different angle positions in the X-ray image diagnosis apparatus illustrated in FIG. 1.
Figure 3B:
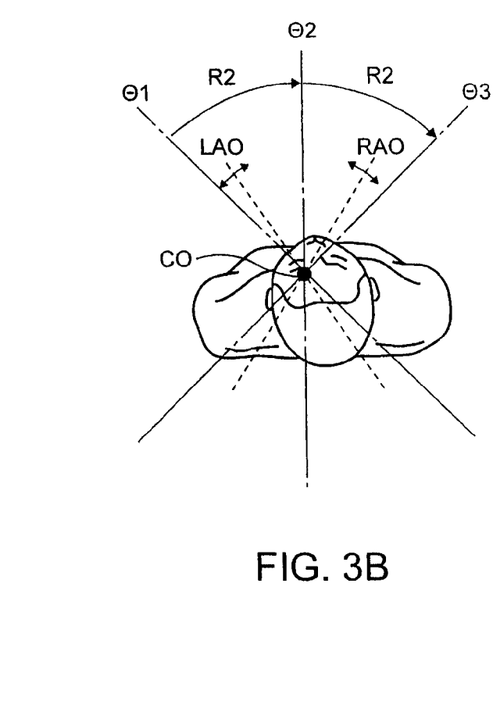
FIG. 3B is an end view illustrating an example of collecting the plurality of two dimensional pixel data at different angle positions θ1, θ2, θ3, respectively by rotating a C-arm in an R2 direction by centering a body axis Z of an object.

With reference to FIGS. 3A and 3B, moving directions of the paired X-ray generating unit 1 and X-ray detecting unit 2 will be explained in accordance with the operations of the C-arm rotating/moving mechanism 32. As shown in FIG. 3A, the X-ray generating unit 1 and the X-ray detecting unit 2 are supported at opposed edge portions of the C-arm 32*a* so as to face each other through an object P laying on the top plate 31*a*. A C-arm central driving mechanism unit 34 moves to rotate the C-arm 32*a* in R1 directions along the arm configuration. Further, the C-arm central driving mechanism unit 34 moves to rotate the C-arm 32*a* in R2 directions around a body axis Z of an object P that passes through a diagnosis portion C0. The C-arm central driving mechanism unit 34 is supported on a prop 35 so as to be able to rotate in the R1 and R2 directions around the rotating axis. The prop 35 is fixed to a floor or a ceiling. Thus, the C-arm 32*a* is moved so as to rotate in the R1 direction that crosses the body axis Z of an object P and also rotate in the R2 direction around the body axis Z of the object P, based on the control signals from the C-arm rotating/moving mechanism 32 to the C-arm central driving mechanism unit 34.

By rotating the C-arm 32*a* in the R1 direction, as illustrated in FIG. 3A, the X-ray generating unit 1 and the X-ray detecting unit 2 moves to rotate in a head direction (Cranial: CRA) and a leg direction (Caudal: CAU) of the object P so that a radiography object portion, for example, a heart of object P, becomes a rotation center (iso-center) C0 of X-ray beams. As illustrated in FIG. 3B, in accordance with a rotation of the C-arm 32*a* in R2 direction, the paired X-ray generating unit 1 and X-ray detecting unit 2 rotates in a right anterior oblique (RAO) direction and a left anterior oblique (LAO) direction around a body axis Z of an object P so that a radiography object portion of the object P becomes an iso-center C0 of X-ray beams. Thus, the paired X-ray generating unit 1 and X-ray detecting unit 2 supported on the C-arm 32*a* rotates in each of the CRA, CAU, RAO and LAO directions in accordance with rotations of the C-arm 32*a* in R1 and R2 directions. By performing such rotating movements, it becomes possible to perform X-ray radiographies at a plurality of angle positions that are appropriate positions and sufficient angle differences. The appropriate positions are such positions that the radiography of the object blood vessel can be performed while avoiding hindrances due to another object, such as bones. The sufficient angle differences are angle difference such that the plurality of pixel data collected at the respective angle positions do not result in occurrence of distortions or errors in the displayed three dimensional pixel data.

The X-ray control unit 42 in high voltage generating unit 4 supplies high voltages to the X-ray tube 11 through the high voltage generating unit 41 based on the radiography conditions for a static image or a motion image. Such radiography conditions are supplied from the system controller 10. To perform an X-ray radiography for a static image, a high voltage from the high voltage generating unit 41 is supplied to the X-ray tube 11 based on control signals supplied from the X-ray control unit 42. When the C-arm 32a is set at a designated radiography angle position by its rotation, a pulse of a high voltage corresponding to a frame rate for a motion image is supplied to the X-ray tube 11 during an irradiation time.

The pixel data generating unit 61 in the pixel data processing unit 6 generates various pixel data from X-ray projection data outputted from the X-ray detecting unit 2 at a line unit. Managing data of radiography conditions are added to the generated pixel data by the pixel data generating unit 61. A plurality of pixel data with added managing data are stored in the pixel data memory unit 62.

When an X-ray is irradiated under a static image radiography condition, the pixel data generating unit 61 generates pixel data of a one frame based on X-ray projection data outputted form the X-ray detecting unit 2. The generated pixel data are stored in the pixel data memory unit 62 with attached managing data of the static image radiography conditions corresponding to the respective pixel data that are supplied from the system controller 10. Further, the generated pixel data are supplied to the three dimensional image data generating unit 66. A three dimensional static image generated in the three dimensional image data generating unit 66 is displayed on a screen in the display unit 8.

When X-rays are irradiated under radiography conditions for a motion image, the pixel data generating unit 61 generates pixel data of frame numbers that corresponds to the frame rate and the irradiation time based on X-ray projection data outputted from the X-ray detecting unit 2 at a plurality of different radiography angles. The system controller 10 attaches a respective radiography condition corresponding to the respective pixel data to the respective pixel data generated at the respective radiography angle positions. Further, vital signal data supplied from the vital data measuring unit 5 are also attached to the respective pixel data. The pixel data with attached respective radiography condition and vital data are stored in the pixel data memory unit 62 and supplied to a three dimensional image data generating unit 66. The three dimensional image data generating unit 66 generates a three dimensional motion image based on a plurality of pixel data having a same phase in the vital data based on the vital data attached to the respective pixel data. The generated three dimensional motion image is outputted to the display unit 8.

Thus, when a three dimensional image display is selected through the operation unit 9 prior to starting an X-ray radiography, pixel data with attached vital data of the same phase are read among a plurality of pixel data generated under the motion image radiography conditions and stored in the pixel data memory unit 62 in the respective radiography angle positions. A three dimensional image data is generated by using the read plurality of pixel data outputted to the display unit 8.

Further, the pixel data are supplied from the pixel data memory unit 62 to the searching unit 7. The searching unit 7 includes a searching unit 71 and a reduced pixel data generating unit 72. The searching unit 71 reads pixel data that are collected through radiography at a plurality of different angle positions and stored with attached vital data in the image data memory unit 62 of the image data processing unit 6. The reduced pixel data generating unit 72 generates reduced pixel data from the searched pixel data in the searching unit 71.

Prior to starting radiography, if a reduced image display is selected through the operation unit 9, the searching unit 71 reads a plurality of two dimensional pixel data among pixel data that are acquired through radiography at a plurality of radiography angle positions and stored in the pixel data memory unit 62. Among the read pixel data, at least more than two sets of pixel data with attached previously designated same phase of vital data are searched. Each set of the searched pixel data is supplied to a reduced pixel data generating unit 72. The reduced pixel data generating unit 72 generates reduced pixel data by reducing each pixel data in the respective sets. The reduced pixel data are generated and outputted depending upon each set. With attached managing data of a particular phase data of vital data, each of the reduced pixel data are displayed on a display unit 8.

The display unit 8 includes a display data generating circuit (not shown) for generating display data by composing both the pixel data outputted from the pixel data processing unit 6 and the reduced pixel data outputted from the pixel data generating unit 61 in the reduced pixel data generating unit 72 in the pixel data searching unit 7 with attached managing data, a converting circuit (not shown) for generating image signals by performing D/A conversion and TV format conversion of the data and a monitor of a liquid crystal display (LCD) or a cathode ray tube (CRT) for displaying the image signal data.

The operation unit 9 is an interactive interface that includes input devices, such as a keyboard, a track ball, a joy stick or a mouse or a display panel and various switches for designating radiography conditions of static image or motion image, selection a three dimensional image display or a reduced image display and for inputting various commands.

In the present embodiment, as the radiography conditions for a motion image, an irradiation time corresponding to n cycles (n is a positive number more than one) of an object P's heart beat cycles is designated. Thus, X-rays are irradiated in the X-ray generating unit 1 during a period of n cycles, i.e., a period of R1-Rn in FIG. 2 at the respective radiography angle positions. The image data generating unit 61 generates image data of frame numbers corresponding to the frame rate during irradiation of the n cycles. In the present embodiment, it is supposed that image data of frame numbers corresponding to irradiated frame rate during three cycles, for example, a period R1-R3 shown in FIG. 2 are generated.

The system controller 10 includes a central processing unit (CPU) and a memory circuit (not shown). The memory circuit in the system controller 10 stores input data, such as command data and radiography conditions supplied from the operation unit 9. The system controller 10 controls entire operations of the apparatus based on the stored input data.

The vital data measuring unit 5 detects vital data through sensors attached on an object. The vital data is processed in the signal processing unit 52 and outputted to the pixel data generating unit 61 in the pixel data processing unit 6 through the system controller 10. Based on the data on radiography angle positions included in the radiography conditions for the motion image, the system controller 10 supplies control signals to the C-arm/top plate mechanism controller 33 in the drive unit 3. In accordance with the control signals, the C-arm/top plate mechanism controller 33 outputs angle position setting signals in order to move the C-arm 32a at the designated plurality of angle positions by driving the C-arm rotation movement mechanism 32. At the same time, the system controller 10 supplies a high voltage to the X-ray tube 11 in the X-ray generating unit 1 by controlling the X-ray control unit 42 in the voltage generating unit 4 during a previously designated period of vital data outputted from the signal processing unit 52 in the vital data measuring unit 5, for example, a period between a first R wave receiving time R1 of an electrocardiogram and a n-th R wave receiving time Rn.

Figure 4:
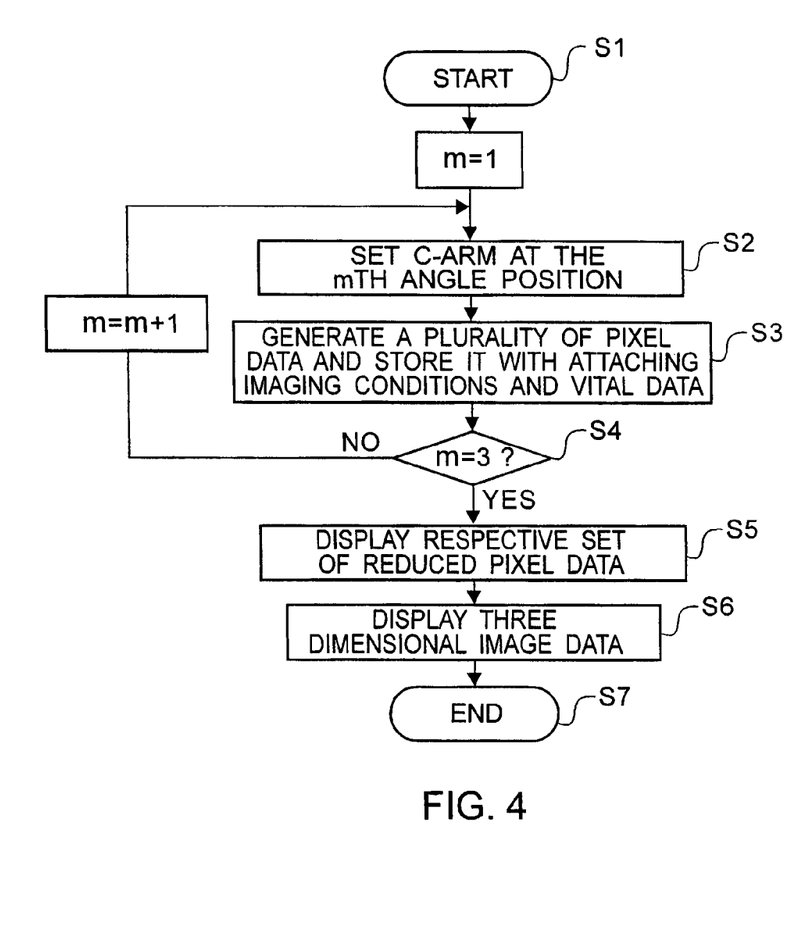
FIG. 4 is a flowchart explaining an embodiment of a method for generating and displaying three dimensional X-ray image data of a moving object in accordance with the present invention.

With reference to the flowchart of FIG. 4, an operation of the embodiment of the X-ray image diagnosis apparatus 100 is explained. Firstly, a radiocontrast agent is injected into the object P and sensors 51 of an electrocardiograph 5 are attached to a body placed on the top plate 31a. In order to diagnose a moving body in the object P, such as a coronary artery, the operation unit 9 designates radiography conditions of motion images and performs a selecting operation for reduced image displays. These inputted operation data are stored in the memory circuit in the system controller 10.

The electrocardiograph 5 supplies vital data of the object P, i.e., ECG signals to the system controller 10. When a display operation of the vital data is performed through the operation unit 9, ECG signals, such as shown in FIG. 2, are displayed on a display unit 8. Next, a phase in the heart beat for performing radiography of the object coronary artery is designated through the operation unit 9. For instance, if an R wave of ECG signals is designated as a radiography phase, the R waves of ECG signals are stored in the memory circuit of the system controller 10 as vital data. Of course, it is possible to designate another phase of ECG signals, such as a Q wave at an end of a diastolic period as a radiography phase for a moving body.

Under a state of these designations, a radiography operation of the X-ray image diagnosis apparatus 100 is started when a start of a radiography is instructed through the operation unit 9 (FIG. 4, step S1).

As illustrated in FIG. 3B, the radiography conditions in the present embodiment are designated for three different radiography angle positions (θ1, θ2, θ3) as radiography positions. The first radiography angle position θ1 is located at a position that rotates in a left anterior oblique (LAO) direction around 45 degrees from a hypothetical axis perpendicular to a body axis Z passing through a object heart portion, i.e., a rotation center, CO. The radiography operation of the moving body object is started from this radiography angle θ1. When X-ray radiography under the frame rate for the motion image at the first radiography angle position has been completed, the paired X-ray generating unit 1 and X-ray detector 2 is moved to a second radiography angle position θ2 by rotating the C-arm 32a in the R2 direction. The second radiography angle θ2 is located on the hypothetical perpendicular axis to the body axis Z passing through the rotation center CO. When radiography operation has completed at the second angle position θ2, the C-arm 32a is rotated in the R2 direction about 45 degrees to a right anterior oblique direction (RAO) so as to move the pair of X-ray generating unit 1 and an X-ray detector 2 to a third radiography angle position θ3. Since a moving angle from the radiography angle θ1 to the second radiography angle θ2 and a moving angle from the second radiography angle θ2 to the three radiography angle θ3 are respectively about 45 degrees, the paired X-ray generating unit 1 and X-ray detector 2 in this embodiment moves about 90 degrees from the first radiography angle position θ1 to the third radiography angle position θ3. Although it is desirable to set the angle positions so as to have a difference of more than a twenty degrees, the present invention is not limited to one particular angle difference. The radiography angle data of the first to the third angles θm (m=1,2,3) in the present embodiment are supplied to the C-arm/top plate mechanism controller 33 in the drive unit 3 through the system controller 10. In accordance with the control signals supplied from the C-arm/top plate controller 33, the C-arm rotating/moving mechanism 32 moves the C-arm 32a in the R2 direction and the paired X-ray generating unit 1 and X-ray detector 2 are set at the m-th angle position θm (m=1,2,3) (FIG. 4, step S2).

When the C-arm 32a is set at the m-th angle position θm by rotating in the R2 direction, the C-arm/top plate mechanism controller 33 outputs a setting signal at the angle θm to the system controller 10. Upon receiving the m-th angle positioning signals from the C-arm/top plate controller 33, the system controller 10 outputs to the X-ray control unit 42 in the high voltage generating unit 4 control signals for irradiating X-ray in order to generate motion images of an object P during a period of two cycles of R waves receiving time that is from a time that the R1 wave in the ECG signals is received by the signal processing unit 52 in the vital data measuring unit 5 to a time that the R3 wave is received. Of course, it is possible to irradiate X-rays during one heart beat cycle of a period between R1 and R2. Further, it is possible to previously calculate a mean time required one cycle among a plurality of heart cycles of an object P, and then irradiate X-rays during the calculated n mean time.

Based on the data on the frame rate and the irradiation time from the X-ray control unit 42, the high voltage generating unit 41 in the high voltage generating unit 4 supplies a high voltage corresponding to the frame rate to the X-ray tube 11 during the designated irradiation time. The X-ray generating unit 1 irradiates X-rays onto the object P in accordance with the high voltage supplied from the high voltage generating unit 41. The X-ray detecting unit 2 generates X-ray projection data which is outputted to the pixel data processing unit 6.

The pixel data generating unit 61 in the pixel data processing unit 6 generates the m-th pixel data of a plurality of frames corresponding to the frame rate among X-ray projection data outputted from the X-ray detecting unit 2. With attached radiography conditions and vital data corresponded to the m-th pixel data that are supplied from the system controller 10, the generated m-th pixel data is stored in the memory unit 62 and also displayed on the display unit 8 (FIG. 4, step S3).

When the angle position setting signal θm reaches m=3 (FIG. 4, step S4, YES), a plurality of sets of the reduced pixel data are displayed (step S5). If the m of the angle setting signal θm has not reached three (3) (FIG. 4, step S4, NO), by setting m=m+1 in the angle setting signal θm, processing returns to the step S2 in order to rotate the C-arm 32a in the R2 direction. It is possible to generate fluoroscopying X-rays of a lower energy than the radiography from the X-ray tube 11 in the X-ray generating unit 1 during a rotating time for setting the C-arm 32a to an (m+1)th angle position θ(m+1) in order to display fluoroscopying pixel data generated in the pixel data generating unit 61 by using such lower fluoroscopying X-rays. Doing this, it becomes possible to confirm injection status of the radiocontrast agent in the object P during the rotation.

When the m of the angle position setting signal θm reaches three (m=3) (step S4, YES), the searching unit 71 in the pixel data searching unit 7 reads the first to the third pixel data with respectively attached R wave data of the previously set ECG signal and angle position data of the first to the third angles θ1, θ2, θ3 from the pixel data memory unit 62.

Figure 5:
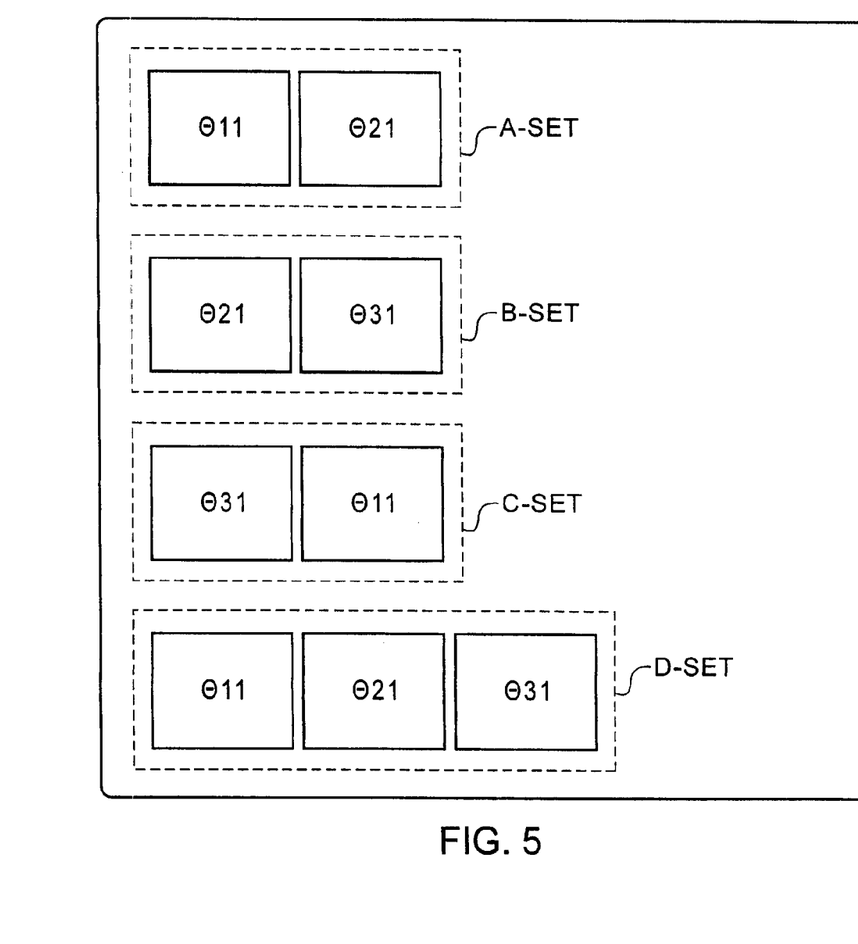
FIG. 5 is an illustration of respective sets of the selected reduced pixel data employed in a displaying method of three dimensional X-ray image data as explained in FIG. 4.

Each set of reduced pixel data is displayed while recognizing the attached attaching R wave data for the respective angle positions. For instance, as illustrated in FIG. 5, a set of two dimensional pixel data θ11 and θ21 with attached data of the first angle θ1 and the second angle θ2 is displayed as an A set of images. An image set of the two dimensional pixel data θ21 and θ31 with attached data of the second and the third angle data θ2, θ3 is displayed as a B set. An image set of the two dimensional pixel data θ31, θ11 with attached third and first angle data θ3 and θ1 is displayed as a C set. Further, an image set of two dimensional pixel data θ11, θ21, θ31 with attached first to third angle data θ1, θ2 and θ3 is displayed as a D set. Each of pixel data is recognized and outputted to the reduced pixel data generating unit 72.

The reduced pixel data generating unit 72 generates reduced pixel data by reducing each of the above-mentioned four sets of pixel data outputted from the searching unit 71. By recognizing each of the generated reduced pixel data, the respective image sets of A set, B set, C set and D set are displayed on the display unit 8 (FIG. 4, step S5). In the screen 81 shown in FIG. 5, each of the reduced pixel data generated in the reduced pixel data generating unit 72 are displayed in a parallel as the respective image sets of A set, B set, C set and D set.

In the images of A set in the screen shown in FIG. 5, each of two dimensional pixel data of the first reduced pixel data θ11 and the second reduced pixel data θ21 generated at the respective the first radiography angle position θ1 and the second radiography angle position θ2 are displayed in parallel. In the images of B set, each of two dimensional pixel data of the second reduced pixel data θ21 and the third reduced pixel data θ31 generated at the respective the second radiography angle positions θ2 and θ3 are displayed in parallel. In the C set of images, two reduced pixel data θ31 and θ11 of two dimensional pixel data generated at the third radiography angle position θ3 and the first radiography angle position θ1 are displayed in parallel. In D set of three reduced pixel data θ11, θ21 and θ31 generated at the respective positions of the radiography angle θ1 to the third radiography angle θ3 are display in parallel. In each of the first to the third reduced pixel data θ11, θ21 and θ31, radiography conditions for the respective reduced pixel data are also displayed.

Among the four image sets of reduced pixel data displayed on the screen 81, the most appropriate image set of reduced pixel data for generating a three dimensional image is selected using the operation unit 9. For instance, if the operation unit 9 selects the reduced pixel data θ11 of the A set, the image data generating unit 61 reads pixel data corresponded to the reduced pixel data θ11 from the pixel data memory unit 62 and displays it on the display unit 8.

Figure 6:
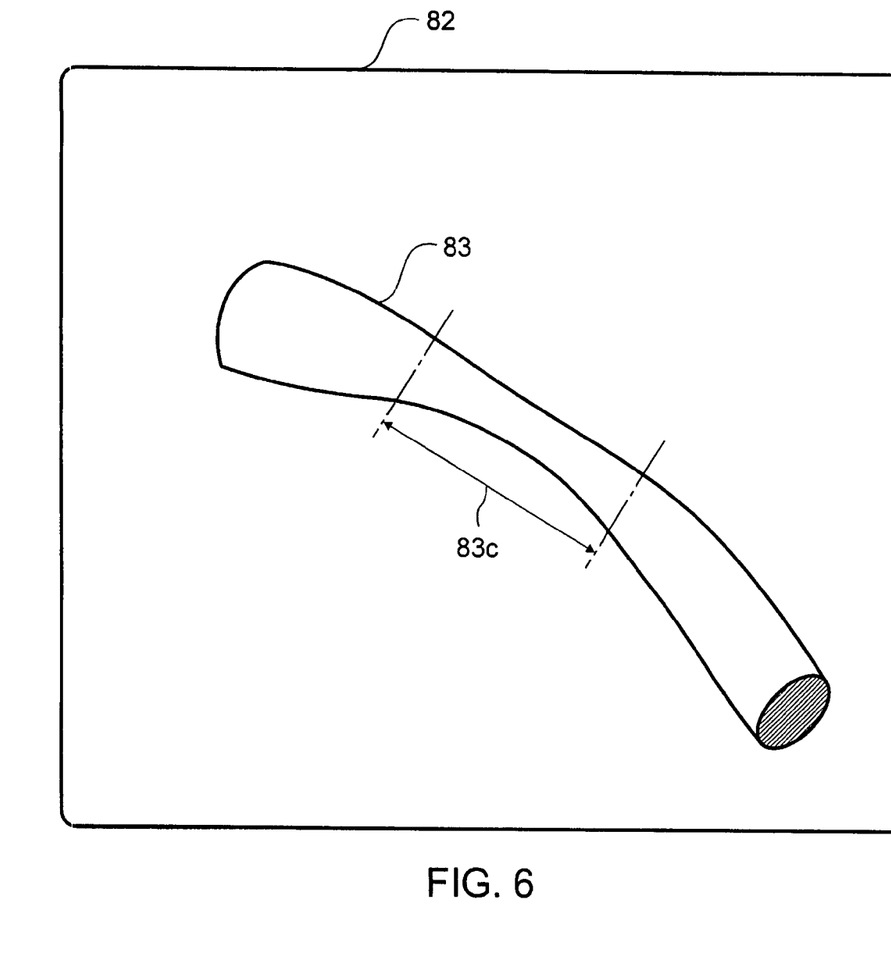
FIG. 6 is an illustration of an example of display of three dimensional image data of a stenosis portion in a coronary artery that are generated and displayed based on a selected set of selected reduced pixel data shown in FIG. 5.

Further, an examining point corresponding to the reduced pixel data θ11 displayed on the display unit 8 is designated on a blood vessel using the operation unit, and then the pixel data generating unit 61 reads each of pixel data corresponding to each of the reduced pixel data θ11 and θ21 from the pixel data memory unit 62. Based on the position data of the pixel data corresponding to the designated reduced pixel data θ11 and the first and second radiography angle data θ1 and θ2, the three dimensional image data generating unit 66 generates three dimensional image data by using the respective read pixel data. As shown in FIG. 6, a three dimensional image data 83 of a blood vessel of a coronary artery is displayed on a screen 82 in the display unit 8 (FIG. 4, step S6). FIG. 6 illustrates an example of display of the three dimensional image data 83 of a blood vessel which includes a stenosis portion 83c.

If a three dimensional image display has been selected through the operation unit 9 prior to start of radiography operations, when the m of the angle position θm setting signal becomes three (m=3) (FIG. 4, step S4, YES), the pixel data generating unit 61 reads image data attached with vital data of R waves and all radiography angle position data (θ1, θ2, θ3) from the image data memory unit 62. By using the read three pixel data, a three dimensional image data is generated and displayed on the display unit 8.

When the operation unit 9 instructs to finish the radiography operation upon confirmation of the two dimensional pixel data or the three dimensional image data 84 displayed on the display unit 8, the system controller instruct an end of radiography operation to the respective X-ray generating unit 1, X-ray detecting unit 2, drive unit 3, high voltage generating unit 4, vital data measuring unit 5, pixel data processing unit 6 and pixel data searching unit 7. In accordance with this instruction, the X-ray image diagnosis apparatus 100 finishes radiography operations (FIG. 4, step S7).

As explained the above, according to the present invention, by setting the C-arm 32a at a plurality of desired angle positions, X-rays are irradiated onto an object P for generating image data during n cycles of the vital data based on periodic vital data of an object P supplied from the vital data measuring unit 5 at each of the designated angle positions. It becomes possible to generate three dimensional image data by using pixel data generated at each of the designated angle positions of the same phase as the previously designated phase. Consequently, a diagnosis or a treatment due to a desired three dimensional image data of an object can be performed rapidly.

The present invention is not limited to the above explained embodiments. For example, it is possible to generate image data by irradiating X-rays onto an object P with the C-arm 32a rotated near the designated angle positions during n cycles of the vital data based on the angle data of the C-arm 32a from the C-arm/top plate mechanism controller 33. The generated pixel data is attached the corresponding angle position data supplied from the C-arm/top plate mechanism controller 33 and vital data from an object P. Thus, it is possible to generate three dimensional image data by using pixel data of the same phase of vital data that are generated at the vicinity of the designated angle positions.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims.

The invention claimed is:

1. An X-ray image diagnosis apparatus comprising:
a paired X-ray generating unit configured to radiate X-rays on an object and X-ray detecting unit configured to detect X-rays penetrated through the object and to generate X-ray projection data;
an angle position setting unit configured to set at least two different radiography angle positions in a successive sequence for imaging the object by moving the paired X-ray generating unit and the X-ray detecting unit;
a controller configured to control moving and performance of radiography operations of the paired X-ray generating unit and X-ray detecting unit based on angle position data supplied from the angle position setting unit and periodic vital data acquired from the object;
a pixel data processing unit configured to generate a plurality of two dimensional pixel data using X-ray projection data supplied from the X-ray detecting unit positioned at the at least two different radiography angle positions during a time corresponding to at least more than one cycle of vital data; and a three dimensional image data generating unit configured to generate three dimensional image data using at least two of the two dimensional pixel data collected at a particular same phase of the vital data among the collected plurality of pixel data at each of the at least two different radiography angle positions generated by the pixel data processing unit;

wherein the at least two different angle positions are sufficiently spaced apart to prevent occurring errors or distortions between two dimensional pixel data collected at the respective angle position of the at least two different angle positions.

2. The X-ray image diagnosis apparatus according to claim 1, wherein the pixel data processing unit generates two dimensional pixel data corresponding to n cycles (n is a positive number greater than one) of a particular phase in a vital data collected at least at two different positions.

3. The X-ray image diagnosis apparatus according to claim 1, further including:

a set searching unit configured to search and combine at least more than two of two dimensional pixel data of a particular phase of the vital data as one set among a plurality of pixel data generated from the pixel data processing unit;

a reduced pixel data generating unit configured to generate reduced pixel data of the respective pixel data in each set of pixel data provided through the set searching unit and to recognize each of the reduced pixel data as a set;

a display unit configured to display each of the reduced pixel data of a set recognized as a set in the reduced pixel data generating unit; and a selection unit configured to select a desired set of the reduced pixel data among a plurality of reduced pixel data displayed on the display unit;

whereby the three dimensional image data generating unit generates three dimensional image data by using pixel data corresponding to the selected set of the reduced pixel data selected by the selection unit.

4. The X-ray image diagnosis apparatus according to claim 3, wherein the pixel data processing unit includes a pixel data memory unit configured to store the generated pixel data; and the pixel data searching unit searches two dimensional pixel data of a particular phase of the vital data that correspond to the at least two different angle positions among the plurality of pixel data stored in the pixel data memory unit.

5. The X-ray image diagnosis apparatus according to claim 1, wherein the paired X-ray generating unit and X-ray detecting unit are supported on a C-arm; and the angle position setting unit includes a C-arm rotating movements controller configured to the paired X-ray generating unit and the X-ray detecting unit at least at two different angle positions.

6. The X-ray image diagnosis apparatus according to claim 1, wherein the X-ray generating unit stops X-ray irradiation during a rotation moving of the paired X-ray generating unit and X-ray detecting unit to a next designated angle position.

7. The X-ray image diagnosis apparatus according to claim 1, wherein the X-ray generating unit irradiates X-rays of a lower energy than an energy irradiated at the at least two different angle positions during movement of the paired X-ray generating unit and the X-ray detecting unit by the angle position setting unit.

8. The X-ray image diagnosis apparatus according to claim 1, further including:

a set searching unit configured to combine at least more than two pixel data as one set among two dimensional pixel data generated in the pixel data processing unit based on a particular same phase of the vital data;

a reduced pixel data generating unit configured to generate reduced pixel data of each set of pixel data combined in the set searching unit and to recognize each of the reduced pixel data as a set;

a display unit configured to display each set of the reduced pixel data recognized; and a selecting unit configured to select a desired set among a plurality of sets displayed on the display unit;

wherein the three dimensional image data generating unit generates three dimensional image data by using pixel data corresponding to reduced pixel data of a set selected by the selecting unit.

9. The X-ray image diagnosis apparatus according to claim 1, wherein the two dimensional pixel data collected at least at two different angle positions are collected in correspondence with R waves in an electrocardiogram of the object.

10. The X-ray image diagnosis apparatus according to claim 1, wherein the two dimensional pixel data collected at least two different angle positions are collected in correspondence with signal data of diastolic end periods.

11. A method for generating image data, comprising:

setting a paired X-ray generating unit for irradiating X-rays onto an object and X-ray detecting unit for detecting X-rays penetrated through the object to generate X-ray projection data at least at two different radiography angle positions;

generating pixel data at the at least two different radiography angle positions in correspondence with n cycles (n is a positive number of more than one) of vital data of an object through a pixel data generating unit using X-ray projection data collected by the X-ray detecting unit set at the at least two different radiography angle positions based on periodic vital data of the object;

generating three dimensional image data using pixel data of a particular phase in the vital data among pixel data generated in the generating step at the at least two different radiography angle positions; and sufficiently spacing apart the at least two different angle positions to prevent occurring errors or distortions between two dimensional pixel data collected at the respective angle position of the at least two different angle positions.

12. A method for generating X-ray image data comprising:

designating a plurality of different radiography angle positions for performing radiography by a paired X-ray source and an X-ray detector through an object;

acquiring vital data of the object in real time;

collecting pixel data for the duration more than at least one cycle of the vital data at a first position of the designated plurality of different radiography angle positions in correspondence with the vital data, rotating the pair of the X-ray source and the X-ray detector to a next angle position so as to collect next pixel data of at least more than one cycle of the vital data in correspondence with the vital data;

selecting a set of pixel data of a particular same phase of the vital data among a plurality of pixel data collected at the plurality of different angle positions;

generating three dimensional image data using the selected set of the pixel data; and sufficiently spacing apart two of the angle positions to prevent occurring errors or distortions between two dimensional pixel data collected at the respective angle position of the two angle positions.

* * * * *